(12) United States Patent
Ziegler et al.

(10) Patent No.: US 10,302,213 B2
(45) Date of Patent: May 28, 2019

(54) FLUIDIC VALVE WITH CONTACTLESS FORCE TRANSMISSION FOR PRESSING TOGETHER STATOR AND ROTOR

(71) Applicant: Agilent Technologies, Inc., Santa Clara, CA (US)

(72) Inventors: Tony Ziegler, Steinfeld (DE); Manfred Berndt, Karlsruhe (DE)

(73) Assignee: Agilent Technologies, Inc., Santa Clara, CA (US)

( * ) Notice: Subject to any disclaimer, the term of this patent is extended or adjusted under 35 U.S.C. 154(b) by 116 days.

(21) Appl. No.: 15/296,929

(22) Filed: Oct. 18, 2016

(65) Prior Publication Data
US 2017/0108140 A1    Apr. 20, 2017

(30) Foreign Application Priority Data

Oct. 19, 2015   (GB) .................................... 1518438.5

(51) Int. Cl.
| | |
|---|---|
| *B01D 15/14* | (2006.01) |
| *B01D 15/24* | (2006.01) |
| *F16K 31/04* | (2006.01) |
| *F16K 31/08* | (2006.01) |

(52) U.S. Cl.
CPC ............ *F16K 31/084* (2013.01); *B01D 15/14* (2013.01); *B01D 15/247* (2013.01); *F16K 31/041* (2013.01)

(58) Field of Classification Search
USPC .................. 251/65, 59, 71; 137/599.07, 544
See application file for complete search history.

(56) References Cited

U.S. PATENT DOCUMENTS

| | | | | |
|---|---|---|---|---|
| 5,842,680 | A | * 12/1998 | Bustamante | ............ F16K 3/085 251/65 |
| 7,284,571 | B2 | * 10/2007 | Ozawa | .................. F16K 31/042 137/625.46 |
| 9,063,114 | B2 | 6/2015 | Wiechers et al. | |
| 2009/0129981 | A1 | 5/2009 | Tokita et al. | |
| 2011/0303304 | A1 | 12/2011 | Tower et al. | |
| 2014/0042351 | A1 | 2/2014 | Wiechers et al. | |
| 2014/0174541 | A1 | 6/2014 | Jencks et al. | |

FOREIGN PATENT DOCUMENTS

| | | |
|---|---|---|
| EP | 1577012 B1 | 11/2014 |
| WO | 2012151080 A1 | 11/2012 |

OTHER PUBLICATIONS

U.K Search Report dated Apr. 19, 2016 from related U.K Application No. GB1518438.5.

* cited by examiner

*Primary Examiner* — Robert K Arundale
*Assistant Examiner* — Daphne M Barry (57) ABSTRACT

A fluidic valve for switching between different fluid coupling states includes a stator having at least one fluidic stator interface, a rotor having at least one fluidic rotor interface, wherein the rotor is rotatable relative to the stator to thereby switch the fluidic valve between a plurality of different fluid coupling states between the at least one fluidic stator interface and the at least one fluidic rotor interface, and a force transmission mechanism configured for pressing the stator and the rotor together by a contactless force transmission to provide for a fluid tight sealing between the stator and the rotor.

16 Claims, 5 Drawing Sheets

Fig. 15

FLUIDIC VALVE WITH CONTACTLESS FORCE TRANSMISSION FOR PRESSING TOGETHER STATOR AND ROTOR

RELATED APPLICATIONS

This application claims the benefit under 35 U.S.C. 119 of GB Patent Application No. 1518438.5, filed Oct. 19, 2015, titled "FLUIDIC VALVE WITH CONTACTLESS FORCE TRANSMISSION FOR PRESSING TOGETHER STATOR AND ROTOR," the content of which is incorporated by reference herein in its entirety.

BACKGROUND ART

The present invention relates to a fluidic valve, to a fluid separation apparatus, and to a method of operating a fluidic valve.

In liquid chromatography, a fluidic sample and an eluent (liquid mobile phase) may be pumped through conduits and a separation unit such as a column in which separation of sample components takes place. The column may comprise a material which is capable of separating different components of the fluidic sample. The separation unit may be connected to other fluidic members (like a sampler or an injector, a detector) by conduits. Before the fluidic sample is introduced into a separation path between a fluid drive unit (in particular a high pressure pump) and the separation unit, a predefined amount of fluidic sample shall be intaken from a sample source (such as a sample container) via an injection needle into a sample loop by a corresponding movement of a piston within a metering device. This usually occurs in the presence of a significantly smaller pressure than what the separation unit is run with. Thereafter, an injector valve is switched so as to introduce the intaken amount of fluidic sample from the sample loop of a metering path into the separation path between fluid drive unit and the separation unit for subsequent separation.

Fluidic valves may be configured as rotatable valves having a stator (which may have one or a plurality of fluid ports) and a rotor (which may have a plurality of grooves for connecting respective ones of the fluid ports) being rotatable with regard to the stator to thereby establish a desired fluid communication state between fluid ports and grooves. In order to be capable to withstand high pressure values of for instance up to 1200 bar in a fluid tight manner, it is necessary to press the rotor against the stator.

Examples of conventional fluidic valves are disclosed in WO 2012/151080, U.S. Pat. No. 9,063,114, US 2014/042351 and US 2014/174541.

However, the required pressing force for establishing the above-mentioned fluid tight connection between stator and rotor conventionally results in a high wear and a limited lifetime of the fluidic valve.

DISCLOSURE

It is an object of the invention to provide a low-wear fluidic valve.

According to an exemplary embodiment of the present invention, a fluidic valve for switching between different fluid coupling states is provided, wherein the fluidic valve comprises a stator having at least one fluidic stator interface (i.e. at least one fluidic interface of the stator by which a fluid can be transported and provided), a rotor having at least one fluidic rotor interface (i.e. at least one fluidic interface of the rotor by which a fluid can be transported and provided), wherein the rotor is rotatable relative to the stator to thereby switch the fluidic valve between a plurality of different fluid coupling states between the at least one fluidic stator interface and the at least one fluidic rotor interface, and a force transmission mechanism configured for pressing the stator and the rotor together by a contactless force transmission to provide for a fluid tight sealing between the stator and the rotor.

According to another exemplary embodiment, a fluid separation apparatus for separating a fluidic sample into a plurality of fractions is provided, the apparatus comprising a fluid drive unit configured for driving a fluid (in particular a liquid and/or a gas, optionally comprising solid particles) comprising a mobile phase (such as a solvent or a solvent composition) and the fluidic sample (i.e. the sample to be actually separated into its fractions) in the mobile phase along a fluidic path, a separation unit arranged within the fluidic path and configured for separating the fluidic sample into the plurality of fractions, and an injector configured for injecting the fluidic sample into the mobile phase in the fluidic path by a fluidic valve having the above-mentioned features.

According to still another exemplary embodiment, a method of switching a fluidic valve between different fluid coupling states is provided, wherein the method comprises rotating a rotor, having at least one fluidic rotor interface, relative to a stator, having at least one fluidic stator interface, to thereby switch the fluidic valve between a plurality of different fluid coupling states between the at least one fluidic stator interface and the at least one fluidic rotor interface, and pressing the stator and the rotor together by a contactless force transmission to provide for a fluid tight sealing between the stator and the rotor.

According to an exemplary embodiment, a pressing force for establishing a fluid tight connection between a stator and a rotor of a fluidic valve so as to set any desired fluidic connection between fluidic rotor interface(s) and fluidic stator interface(s) substantially without leakage is advantageously applied by a contactless force transmission mechanism. This means that the pressing force is applied using at least one force transmission element (such as a floating force transmission magnet) which does not have permanent contact with at least one other force transmission element and is therefore capable of contributing to the pressing force in a self-adjustable manner. In other words, the contactless force transmission can be accomplished in such a way that any potential axial misalignment can be self-sufficiently balanced out partly or entirely by the contactlessly operating force transmission element. Unlike conventional approaches, such a contactless force transmission mechanism does not suffer from high wear between rotor and stator and consequently short lifetime of the fluidic valve as a whole, since any redundant dimensioning or overdetermination is prevented or overcome by the contactlessly operating force transmission element being movably mounted for actual misalignment force equilibration. This results in a fluidic valve having reduced wear and increased lifetime. Consequently, a smaller pressing force is sufficient to ensure fluid-tightness even under high fluid pressure conditions. Due to the self-alignment capability of the force transmission mechanism, the tendency of leakage as a consequence of a non-perfect axial parallel alignment between a contact surface of the stator and a contact surface of the rotor is strongly suppressed. This allows to obtain a low-friction fluid tight system with smaller contact pressure as compared to conventional approaches.

In the following, further embodiments of the fluidic valve, the fluid separation apparatus, and the method will be explained.

In an embodiment, the force transmission mechanism is mounted in the fluidic valve so as to be capable of performing an equilibration motion for at least partially equilibrating a misalignment force (in particular due to an axial misalignment between the rotor and stator) acting between the stator and the rotor. The axial direction may correspond to a rotation axis of the rotor and may, in a desired operation state of the fluidic valve, corresponding to a normal direction of a planar contact surface of the stator contacting a corresponding planar contact surface of the rotor. However, axial misalignment between stator and rotor may temporarily occur under undesired circumstances which means that the two contact surfaces may be temporarily not in perfect parallel alignment to one another, resulting in temporarily high forces acting between these contact surfaces and consequently wear. According to the described embodiment however, the force transmission mechanism comprises an intrinsic self-alignment capability which ensures that such misalignment forces can be at least partially equilibrated or balanced out by the force transmission mechanism itself, which also contributes to the generation of the pressing force.

In an embodiment, the force transmission mechanism comprises (two or more) cooperating force transmission elements or bodies configured for generating a pressing force for pressing the stator and the rotor together. These force transmission elements may be configured so as to generate a mutual force operable for pressing the rotor and the stator together. As long as the generated force is produced in a contactless way between the force transmission elements, the type of force can broadly vary. For instance, the cooperating force transmission elements may generate an attracting or a repelling force which, in combination with a corresponding spatial arrangement of the force transmission elements, provides for the desired pressing force between stator and rotor. Such a force may be a magnetostatic force, an electrostatic force, an electrodynamic force, etc. Preferably, the force transmission mechanism is a purely permanent magnetic force transmission mechanism, since this allows, in a maintenance free manner, to generate strong forces with small space consumption and low technical effort. The absolute value of the repelling forces may be only 5% to 10% smaller than the absolute value of the attracting forces.

In one embodiment (see for example FIG. 14), a low friction interface is embodied as a first low friction body on a foremost force transmitting element and, in contact therewith, a second low friction body on a seal member (more particularly on a seal keeper thereof). The described embodiment has the advantage that a dry coupling may be accomplished. It should however be said that, although a dry coupling configuration is possible and advantageous, the optional additional use of oil or grease or some other lubricant for further improving the low friction performance is possible. In the case of the embodiment of FIG. 15, oil and/or grease or some other lubricant can be permanently present and may be dispensable in operation as required. In such an embodiment (see for example FIG. 15), the low friction interface can be embodied as a low friction body on the foremost force transmitting element and, in contact therewith, a roller bearing between the low friction body and the seal member (more particularly on a seal keeper thereof). The provision of such a low friction interface has the advantage to allow operation of the fluidic valve with the seal member and the force transmission mechanism freely moving relative to one another, while it is simultaneously possible to accomplish such an operation with low energy consumption and low generation of heat as well as low wear.

In an embodiment, all force transmission elements are mounted in the rotor. Corresponding force transmission elements may be arranged so that they generate a mutually repelling force which presses the impacted contact surface of the rotor against the corresponding contact surface of the stator. Since force values (such as a magnetic force value, an electric force value, etc.) between force transmission elements become weaker with increasing distance, it is desirable to mount all force transmitting elements close together so as to keep dimensioning and force values generated by the force transmission elements as small as possible. This also reduces optional efforts in terms of shielding such forces with regard to an environment of the fluidic valve. As an alternative to the described embodiment, it is however also possible that all force transmission elements are mounted in the stator, or that part of the force transmission elements is mounted in or around the stator and another part of the force transmission elements is mounted in the rotor.

In an embodiment, the force transmission elements are configured as magnets, in particular as permanent magnets which involves only small implementation effort (alternatively, the magnets may be embodied as activatable and adjustable electromagnets). The configuration of the force transmission element as magnets is advantageous, since it allows with reasonable effort for a compact and powerful force transmission mechanism. Furthermore, magnetic forces are perfectly compatible with the requirements of a contactless force transmission.

In an embodiment, the magnets are arranged for generating the pressing force by a mutually repelling magnetic force between the magnets. This repelling magnetic force advantageously presses the contact surface of the rotor against the contact surface of the stator and allows to mount both magnets in the rotor (alternatively to mount both magnets in the stator), thereby allowing for a compact arrangement with reasonably small forces. Alternatively, an attracting magnetic force between two magnetic force elements may be established which may be accomplished by mounting one of the magnetic force elements in the rotor and the other one in the stator.

In an embodiment, the magnets are arranged with an axial gap in between (in particular in a configuration with one magnet behind the other in axial direction), the gap being maintained by a repelling magnetic force between the magnets. This axial gap allows the magnetic system temporarily to slightly move out of a rest position, whereby exerted forces can be balanced so as to be capable of reacting on and at least partially equilibrating axial misalignment forces between stator and rotor.

In an embodiment, at least one of the force transmission elements is fixedly mounted, in particular in or around the rotor. At least one other of the force transmission elements may be floatingly mounted, in particular in or around the rotor. The fixedly mounted force transmission element may for example be coupled or connected to a valve housing, in particular a rotor housing. The floatingly mounted force transmission element may be movably mounted in the valve housing, in particular rotor housing, so as to be able to carry out a certain equilibration motion in the event of parasitic misalignment forces between stator and rotor.

In an embodiment, the fixedly mounted force transmission element is mounted axially more remotely from the stator than the floatingly mounted force transmission element. More specifically, the floatingly mounted force transmission element may be coupled or connected to the contact surface of the rotor. Thus, the impact on the contact surface of the rotor may be rendered high in case of a close connection of the floatingly mounted force transmission element.

In an embodiment, the fluidic valve comprises a resilient element arranged between the fixedly mounted force transmission element and a casing of the rotor. For example, such a resilient element may be embodied as a spring (such as a metal spring, an elastomer spring, a plastic spring), or may be a rubber body or a gel cushion. As a resilient element, also at least one further magnet or magnet pair (with or without separator) may be provided. At least two magnet pairs with a separator in between increase magnetic forces as well as the movable way of such a resilient element and have turned out to be particularly efficient. Such a resilient element may be mounted and configured to tilt or pivot in the event of an axial misalignment or when the above-mentioned gap between a front force transmission element and a rear force transmission element is no longer plane-parallel or coplanar, to thereby contribute to the equilibration and reduction of wear of the fluidic valve. Provisions may be taken to maintain the gap with a constant dimension.

In an embodiment, the fluidic valve comprises a rotor shaft configured for rotating at least part of the rotor and extending through the force transmission elements. Hence, the force transmission elements may be configured as annular bodies each having a through hole through which the rotatable rotor shaft extends towards the contact surface of the rotor. A back end of the rotatable shaft may be connected to a driving unit such as an electric motor.

In an embodiment, the rotor shaft is configured as one of the group consisting of a solid shaft, a hollow shaft, and a flexible shaft. A solid shaft may provide for a robust configuration. A hollow shaft may provide for a lightweight configuration. A flexible shaft may provide an additional contribution to at least partially equilibrating axial misalignment forces, in addition to the force transmission mechanism.

In an embodiment, the fluidic valve comprises a rotatable lateral gear mechanism configured for rotating at least part of the rotor and being arranged laterally (or side by side in relation to the rotation axis) of the force transmission elements. As an alternative to a shaft extending through the force transmission elements, it is possible that the drive unit and the gear mechanism are juxtaposed parallel to a rotation axis of the rotor. This allows a free design of the force transmission elements without any limitations due to the close presence of the shaft.

In an embodiment, the rotatable lateral gear mechanism is configured as one of the group consisting of a gear wheel and a tooth belt. A gear wheel can be implemented as a solid disk-shaped body having a plurality of teeth along a perimeter thereof, wherein these teeth may engage corresponding teeth of a cooperating rotor component. A tooth belt many implemented as a driven belt having a plurality of teeth along a perimeter thereof, wherein these teeth may engage corresponding teeth of a cooperating rotor component.

In an embodiment, adjacent ones of the force transmission elements are axially spaced from one another by a gap and are configured with a mutual form closure design so as to counteract or suppress axial misalignment between the force transmission elements. Such a mutual form closure design may be configured in a way which prevents or limits or disables undesired temporary tilting of the force transmission elements with regard to one another and with regard to the above described axial direction. With the described mutual form closure design (for instance a protrusion of one of the force transmission elements extending into a recess of another of the force transmission elements) it may be accomplished that the force transmission magnets act in a self-centering way.

In an embodiment, the fluidic valve comprises a force adjustment mechanism configured for adjusting a pressing force provided by the force transmission mechanism. For instance, an actual pressing force may be measured by a pressure sensor of the force adjustment mechanism within the fluidic valve, in particular within the rotor. An actuator of the force adjustment mechanism, for instance a piezo actuator, within the fluidic valve, in particular within the rotor, can then adjust the pressing force based on a comparison between the measured force and a predetermined target pressing force. By such a force adjustment mechanism, it is possible to readjust the fluidic valve to thereby compensate aging effects (such as a reduced magnetic force provided by a permanent magnet due to slight demagnetization over time), etc.

In an embodiment, the at least one fluidic stator interface (or the at least one fluidic rotor interface) is configured as at least one fluidic port. In an embodiment, the at least one fluidic rotor interface (or the at least one fluidic stator interface) is configured as at least one fluidic groove. The fluidic valve may hence be equipped with a stator which may have one or a plurality of fluid ports (connected or to be connected to one or more further fluidic components, depending on an application) and a rotor which may have a plurality of grooves for connecting or bridging respective ones of the fluid ports. By rotating the rotor with regard to the stator, it is then possible to establish a desired fluid communication state between fluid ports and grooves. In a fluid coupling state, a respective groove may bridge two respective fluid ports. In a fluid decoupling state, a respective groove may be arranged apart from the two respective fluid ports.

Embodiments of the above described fluid valve may be implemented in conventionally available HPLC systems, such as the Agilent 1200 Series Rapid Resolution LC system or the Agilent 1100 HPLC series (both provided by the applicant Agilent Technologies—see www.agilent.com—which shall be incorporated herein by reference).

One embodiment of a fluid separation apparatus, in which one or more of the above described fluidic valves may be implemented, comprises a pumping apparatus as fluid drive unit or mobile phase drive having a pump piston for reciprocation in a pump working chamber to compress liquid in the pump working chamber to a high pressure at which compressibility of the liquid becomes noticeable. This pumping apparatus may be configured to know (by means of operator's input, notification from another module of the instrument or similar) or elsewise derive solvent properties, which may be used to represent or retrieve actual thermal properties of fluidic content, which is anticipated to be in a sampling apparatus.

The separation unit of the fluid separation apparatus preferably comprises a chromatographic column (see for instance the website at en.wikipedia.org/wiki/Column_chromatography) providing the stationary phase. The column may be a glass or steel tube (for instance with a diameter from 50 μm to 5 mm and a length of 1 cm to 1 m) or a microfluidic column (as disclosed for instance in EP 1577012 or the Agilent 1200 Series HPLC-Chip/MS System provided by the applicant Agilent Technologies). The individual components are retained by the stationary phase differently and at least partly separate from each other while they are propagating at different speeds through the column with the eluent. At the end of the column they elute one at a time or at least not entirely simultaneously. During the entire chromatography process the eluent may be also collected in a series of fractions. The stationary phase or adsorbent in column chromatography usually is a solid material. The most common stationary phase for column chromatography is silica gel, surface modified silica gel, followed by alumina. Cellulose powder has often been used in the past. Also possible are ion exchange chromatography, reversed-phase chromatography (RP), affinity chromatography or expanded bed adsorption (EBA). The stationary phases are usually finely ground powders or gels and/or are microporous for an increased surface.

The mobile phase (or eluent) can be a pure solvent or a mixture of different solvents (such as water and an organic solvent such as ACN, acetonitrile). It can be chosen for instance to minimize the retention of the compounds of interest and/or the amount of mobile phase to run the chromatography. The mobile phase can also be chosen so that the different compounds or fractions of the fluidic sample can be separated effectively. The mobile phase may comprise an organic solvent like for instance methanol or acetonitrile, often diluted with water. For gradient operation water and organic is delivered in separate bottles, from which the gradient pump delivers a programmed blend to the system. Other commonly used solvents may be isopropanol, tetrahydrofuran (THF), hexane, ethanol and/or any combination thereof or any combination of these with aforementioned solvents.

The fluidic sample may comprise but is not limited to any type of process liquid, natural samples like juice, body fluids like plasma, etc., or it may be the result of a reaction like from a fermentation broth.

The pressure, as generated by the fluid drive unit, in the mobile phase may range from 2-200 MPa (20 to 2000 bar), in particular 10-150 MPa (100 to 1500 bar), and more particularly 50-120 MPa (500 to 1200 bar).

The fluid separation apparatus, for instance an HPLC system, may further comprise a detector for detecting separated compounds of the fluidic sample, a fractionating unit for outputting separated compounds of the fluidic sample, or any combination thereof. Further details of such an HPLC system are disclosed with respect to the Agilent 1200 Series Rapid Resolution LC system or the Agilent 1100 HPLC series, both provided by the applicant Agilent Technologies, under www.agilent.com which shall be incorporated herein by reference.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in or by the control unit.

BRIEF DESCRIPTION OF DRAWINGS

Other objects and many of the attendant advantages of embodiments of the present invention will be readily appreciated and become better understood by reference to the following more detailed description of embodiments in connection with the accompanying drawings. Features that are substantially or functionally equal or similar will be referred to by the same reference signs.

The illustration in the drawing is schematic.

DETAILED DESCRIPTION

Before describing the figures in further detail, some basic considerations of the present invention will be summarized based on which exemplary embodiments have been developed.

According to an exemplary embodiment of the invention, a fluidic valve with a valve pod is provided using magnetic repulsion forces for pressing a rotor against a stator, thereby accomplishing fluid tightness with reasonable pressing forces. With such a valve architecture, it is possible to construct a valve pod capable of holding more than 1200 bar of pressure acting on a rotor seal. Advantageously in particular for fast switching, the magnets do not turn, so only the rod, rotor seal keeper and the rotor seal itself contribute to inertia. Furthermore, such a fluidic valve may operate in a self-adjusting way, so that no adjusting screws or the like are required. A characteristic magnet force line can be configured to be softer in comparison to that of conventional disc spring packages.

More generally, a fluidic valve implementing a contactless operating force transmission mechanism according to an exemplary embodiment of the invention has several technical advantages over purely spring loaded valve pod setups, because such an embodiment implements only very low friction, since a force adjust magnet can be contact-free on one side. This may allow to use smaller motors or a slimmer propulsion rod to further reduce inertia of the system. By the use of magnets for configuring the force transmission mechanism, it is possible to construct a self-aligning magnet system. Due to this self-aligning mechanism, sealing forces can be significantly reduced, for instance to only half or one third of conventional systems using spring discs. Less torsion can be exerted on the propulsion rod, hence the swinging motion along the axis after switching may calm sooner, which may result in less grinding. A force adjustment magnet may be arranged to follow a rotor seal keeper automatically with a flat force per distance characteristic. Moreover, a grease-free or at least grease reduced valve pod may be provided as a result of the contactless force transmission architecture.

Due to temporarily increased wear or a larger sinking in of the rotor seal, a force adjust magnet may move farther up. If this following distance becomes too large (i.e. magnetic forces decrease too greatly), it may be advantageous to introduce an additional spring element to create a well-balanced system "spring-magnet-magnet".

Figure 1:
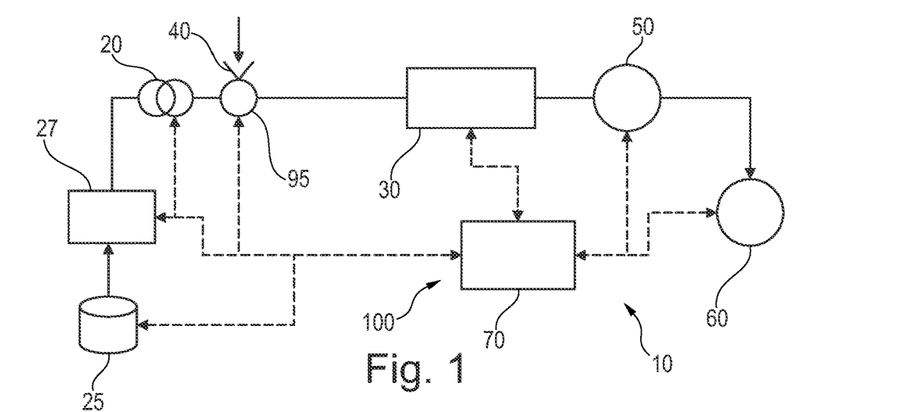
FIG. 1 shows a liquid separation apparatus in accordance with embodiments of the present invention, particularly used in high performance liquid chromatography (HPLC).

Referring now in greater detail to the drawings, FIG. 1 depicts a general schematic of a liquid separation system as example for a fluid separation apparatus 10 according to an exemplary embodiment of the invention. A pump 20 receives a mobile phase from a solvent supply 25, typically via a degasser 27, which degases and thus reduces the amount of dissolved gases in the mobile phase. The pump 20—as a mobile phase drive or fluid drive unit—drives the mobile phase through a separating device 30 (such as a chromatographic column) comprising a stationary phase. An injector or sampling unit 40, implementing a fluidic valve 95, can be provided between the pump 20 and the separating device 30 in order to subject or add (often referred to as sample introduction) a sample fluid into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the fluid separation apparatus 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump 20). The data processing unit 70 might also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sampling unit 40 (e.g. controlling sample injection or synchronization of sample injection with operating conditions of the pump 20). The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provide data back.

Configurations of the fluidic valve 95 according to exemplary embodiments of the invention will be described in the following in further detail referring to FIG. 2 to FIG. 7 and FIG. 10 to FIG. 13.

Figure 2:
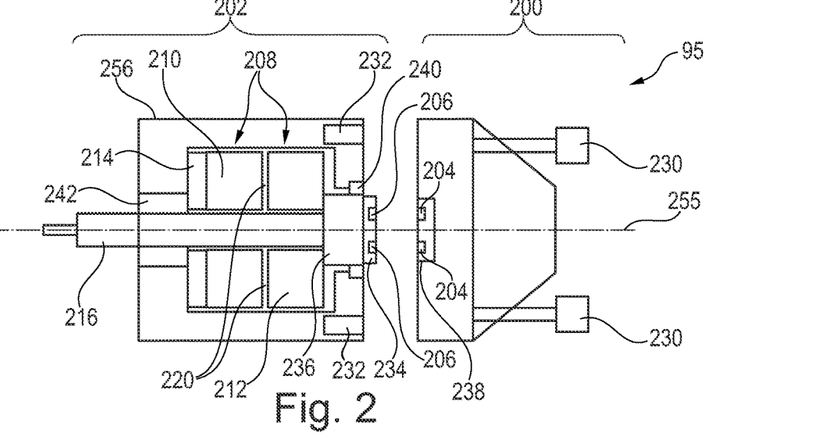
FIG. 2 illustrates a cross-sectional view of a fluidic valve according to an exemplary embodiment of the invention.

FIG. 2 illustrates a cross-sectional view of a fluidic valve 95 according to an exemplary embodiment of the invention.

The fluidic valve 95 is configured for switching between different fluid coupling states and comprises a stator 200 and a rotor 202. For mechanically connecting the stator 200 with the rotor 202, fastening elements 230 (such as screws) of the stator 200 are fastened with (such as screwed into) corresponding fastening elements 232 (such as a screw hole or an inner thread) of the rotor 202. The stator 200 has a contact surface with a plurality of fluidic stator interfaces 204 embodied as fluidic ports formed to extend into the contact surface of the stator 200. Correspondingly, the rotor 202 has a plurality of fluidic rotor interfaces 206 embodied as grooves in a contact surface of the rotor 202. For the sake of simplicity, the fluidic stator interfaces 204 as well as the fluidic rotor interfaces 206 are shown in FIG. 2 only, but can be arranged at corresponding positions in each of the embodiments of FIG. 3 to FIG. 7 and FIG. 10 to FIG. 13. Upon connecting the stator 200 with the rotor 202, their contact surfaces are brought into contact with one another so that a fluid tight connection between the stator 200 and the rotor 202 and a fluidic coupling between respective ones of the fluidic rotor interfaces 206 and the fluidic stator interfaces 204 is established. A rotatable inner portion of the rotor 202 is rotatable relative to the stator 200 around a rotation axis oriented along an axial direction 255 (which is ideally rectangular with regard to a stator face) to thereby switch the fluidic valve 95 between a plurality of different fluid coupling states between the fluidic stator interfaces 204 and the fluidic rotor interfaces 206. A force transmission mechanism 208, which will be described in the following in further detail, is implemented in the fluidic valve 95 and is configured for pressing the stator 200 and the rotor 202 together by a contactless force transmission to provide for a fluid tight sealing between the stator 200 and the rotor 202 even under high fluid pressure conditions.

More specifically, the force transmission mechanism 208 is mounted in the fluidic valve 95 so as to be capable of performing an equilibration motion for at least partially equilibrating a misalignment force which may result from an axial misalignment between the rotor 202 and stator 200. The force transmission mechanism 208 comprises two cooperating force transmission elements 210, 212 configured for generating the pressing force for pressing the stator 200 and the rotor 202 together. According to the embodiment of FIG. 2, both force transmission elements 210, 212 are configured as a permanent magnets which are mounted within a static casing 256 of the rotor 202. The casing 256 can be configured so as to shield the magnetic field generated by the magnetic force transmission elements 210, 212 with regard to an environment of the fluidic valve 95. For this purpose, the casing (or the inside of the casing) 256 may be made of a metallic material such as Mu-metal/permalloy or another ferromagnetic material (for static magnetic fields) or a dipole material like copper or silver (for changing electromagnetic fields). Alternatively, the casing 256 may be made of sufficiently thick plastic material such as polyetheretherketone (PEEK).

The magnetic force transmission elements 210, 212 are arranged for generating the pressing force by a mutually repelling magnetic force between them. Furthermore, the magnets are arranged with an axial gap 220 in between them, wherein the gap 220 is maintained by the repelling magnetic force between the magnets. A rear one of the force transmission elements 210, 212, i.e. force transmission element 210, is fixedly mounted in the rotor 202. The other one of the force transmission elements 210, 212, i.e. force transmission element 212, is floatingly mounted in the casing 256. Thus, the fixedly mounted force transmission element 210 (which may also be denoted as base magnet) is mounted axially more remotely from the stator 200 than the floatingly mounted force transmission element 212. A resilient element 214, which can be embodied as a spring or spring package, may be arranged between the fixedly mounted force transmission element 210 and the casing 256 of the rotor 202. Thus, an increasing gap between force transmission elements 210, 212 due to such as wear or settling of materials (above force transmission element 212) can at least partially be compensated by the resilient element 214, axially repositioning force transmission elements 210, 212, while a slight misalignment between force transmission elements 210, 212 is corrected by the magnetic field between the force transmission elements 210, 212. A response of the fluidic valve 95 to such a misalignment is therefore a balancing motion of the floatingly mounted force transmission element 212 which at least partly corrects or compensates for such a misalignment and drives back the system into equilibration. Although the fixedly mounted force transmission element 210 cannot perform a free equilibration motion, its coupling to the casing 256 via the resilient element 214 provides also the fixedly mounted force transmission element 210 with a limited misalignment balancing capability. The resilient element 214 is configured for performing a slight tilting motion in the event of the gap 220 leaving its plane-parallel or coplanar configuration.

The fluidic valve 95 furthermore comprises a propulsion rod or rotor shaft 216 which is driven by an electric motor (not shown in FIG. 2) and is configured for rotating a rotatably mounted inner part of the rotor 202. The rotor shaft 216 axially extends through central through holes in the annular force transmission elements 210, 212. To reduce weight, the rotor shaft 216 may be configured as a hollow shaft.

The contactless operation of the force transmission mechanism 208 for generating the pressing force for contacting rotor 202 and stator 200 in a high pressure fluid tight manner according to FIG. 2 has the advantage that even moderate contact forces (of for instance less than 1000 N) may be sufficient to prevent leakage even at a fluidic pressure of 1200 bar while simultaneously keeping friction and wear at a low level and thereby ensuring a high lifetime of the fluidic valve 95. This can be accomplished due to the provision of the self-aligning, misalignment suppressing configuration of the force transmission mechanism 208. Any overdetermination, which conventionally involves the risk of high wear due to misalignment between stator 200 and rotor 202 can therefore be avoided. In other words, the pressing force can be used substantially completely for sealing, rather than for equilibrating overdetermination (by deformation).

In addition to the already described elements of the fluidic valve 95, a rotor seal 234 (such as a sealing platelet, for instance made of plastic, coated steel, coated hard metal (such as tungsten carbide) or ceramic) is provided which defines the contact surface of the rotor 202 and which accommodates the rotor fluidic interfaces 206. The rotor seal 234 may sealingly cooperate with a sealing inlay 238 (such as a sealing platelet, for instance made of ceramic) defining the contact surface and forming part of the stator 200. A rotor seal keeper 236 bridges the floatingly mounted force transmission element 212 and the rotor seal 234 and may be connected to the floatingly mounted force transmission element 212. Thus, according to FIG. 2, the floatingly mounted force transmission element 212 only touches and presses the rotor seal keeper 236. More generally, the rotor seal keeper 236 may or may not be connected to the force adjustment magnet (i.e. the floatingly mounted force transmission element 212), for instance depending on friction, torque and inertia requirements. Furthermore, a front guide part 240 (which may also be a ball or roller bearing or any combined axial and radial bearing) promotes a guided operation of the rotor 202. Correspondingly, a rear guide part 242 (which may also be a ball or roller bearing or any combined axial and/or radial bearing) promotes as well a guided operation of the rotor 202. Thus, the embodiment of FIG. 2 relates to a rear and front guided propulsion rod or rotor shaft 216.

Figure 3:
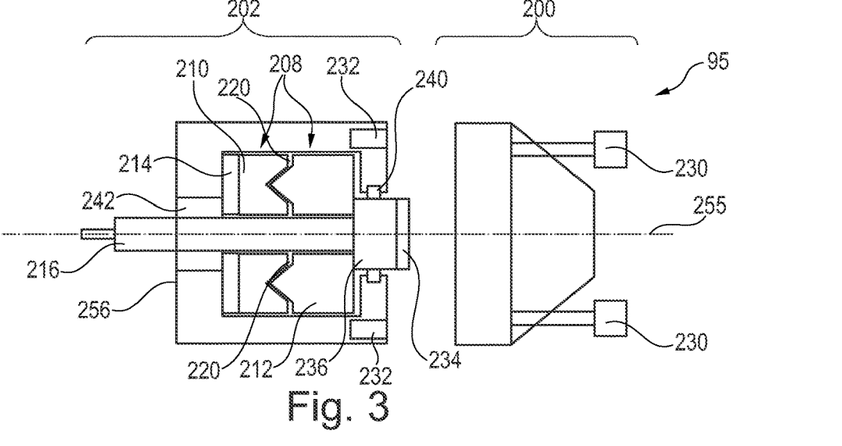
FIG. 3 illustrates a cross-sectional view of a fluidic valve according to another exemplary embodiment of the invention.

FIG. 3 illustrates a cross-sectional view of a fluidic valve 95 according to another exemplary embodiment of the invention.

The embodiment of FIG. 3 differs from the embodiment of FIG. 2 in particular in that the adjacent force transmission elements 210, 212 being axially spaced from one another by gap 220 are configured in FIG. 3 with a mutual form closure design so as to counteract axial misalignment between the force transmission elements 210, 212. Hence, one of the force transmission elements 212 is provided with a protrusion engaged by a recess of the other force transmission element 210 with the gap 220 in between. This promotes a self-centering of the magnetic force transmission elements 210, 212.

Figure 4:
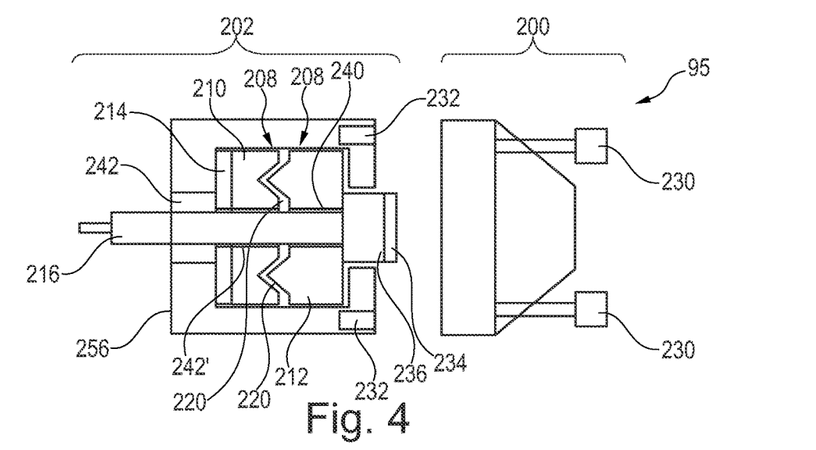
FIG. 4 illustrates a cross-sectional view of a fluidic valve according to another exemplary embodiment of the invention.

FIG. 4 illustrates a cross-sectional view of a fluidic valve 95 according to still another exemplary embodiment of the invention.

The embodiment of FIG. 4 differs from the embodiment of FIG. 3 in particular in that, according to FIG. 4, the self-aligning magnet in form of the floatingly mounted force transmission element 212 touches not only the rotor seal keeper 236 but also the rotor shaft 216 or propulsion rod. According to FIG. 4, the guide part 240 is now implemented at the force adjust magnet or floatingly mounted force transmission element 212. Reference numeral 242' indicates an alternative to the guide part 242.

Figure 5:
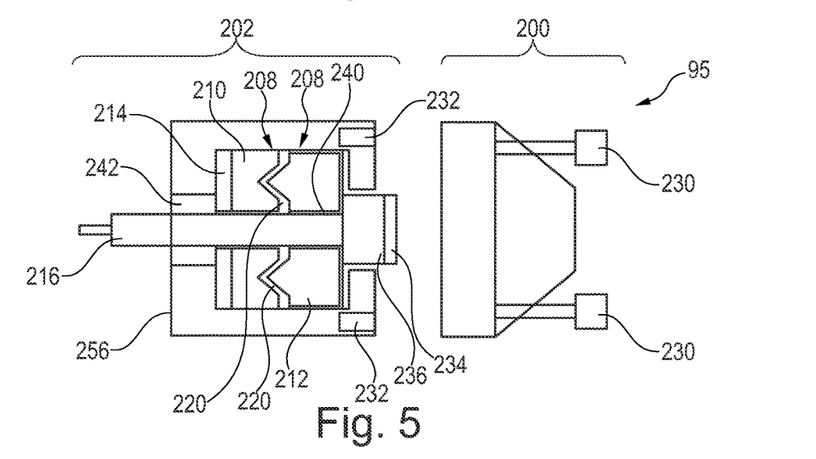
FIG. 5 illustrates a cross-sectional view of a fluidic valve according to another exemplary embodiment of the invention.

FIG. 5 illustrates a cross-sectional view of a fluidic valve 95 according to still another exemplary embodiment of the invention.

The embodiment of FIG. 5 differs from the embodiment of FIG. 4 in particular in that, according to FIG. 5, the self-aligning magnet or floatingly mounted force transmission element 212 additionally touches the wall or casing 256 of the containment as a guiding.

Figure 6:
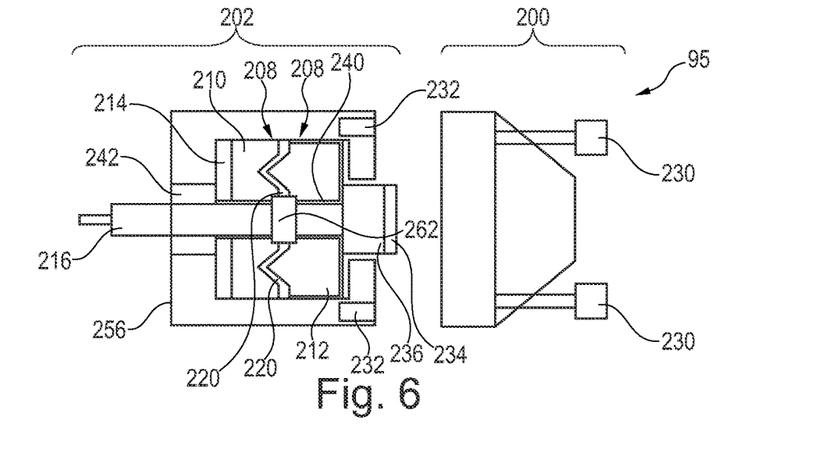
FIG. 6 illustrates a cross-sectional view of a fluidic valve according to another exemplary embodiment of the invention.

FIG. 6 illustrates a cross-sectional view of a fluidic valve 95 according to yet another exemplary embodiment of the invention.

The embodiment of FIG. 6 differs from the embodiment of FIG. 5 in particular in that the embodiment of FIG. 6 additionally comprises a flex coupling 262 which may be advantageous in case of a rigid rotor shaft 216. Alternatively, the rotor shaft 216 or propulsion axis can be solid, hollow or intrinsically flexible.

Figure 7:
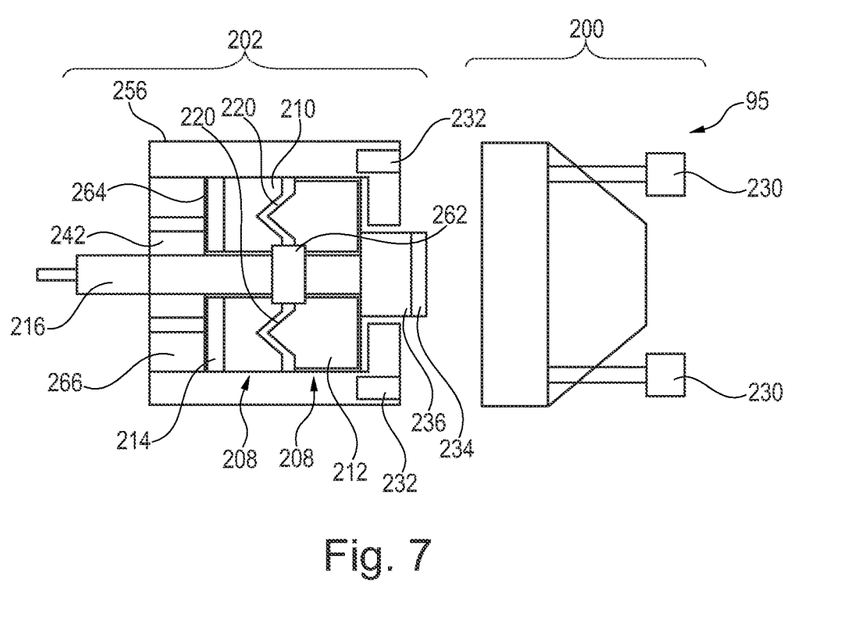
FIG. 7 illustrates a cross-sectional view of a fluidic valve according to another exemplary embodiment of the invention.

FIG. 7 illustrates a cross-sectional view of a fluidic valve 95 according to yet another exemplary embodiment of the invention.

The embodiment of FIG. 7 differs from the embodiment of FIG. 6 in particular in that FIG. 7 additionally comprises a force adjustment mechanism 264, 266 configured for adjusting a pressing force provided by the force transmission mechanism 208. More specifically, the force adjustment mechanism 264, 266 comprises a pressure sensor 264 (alternatively a force sensor) configured for determining the pressure at its mounting position. An actuator 266 adjusts the sealing force, for instance by an electric motor, a pneumatic mechanism, a piezo element, etc. if the measured pressure indicates a deviation from a target pressure value.

It should be mentioned that each of the embodiments of FIG. 3 to FIG. 7 can also be implemented without protrusions and recesses and/or with equally thick magnets (in particular in terms of north- and south-sections).

Figure 8:
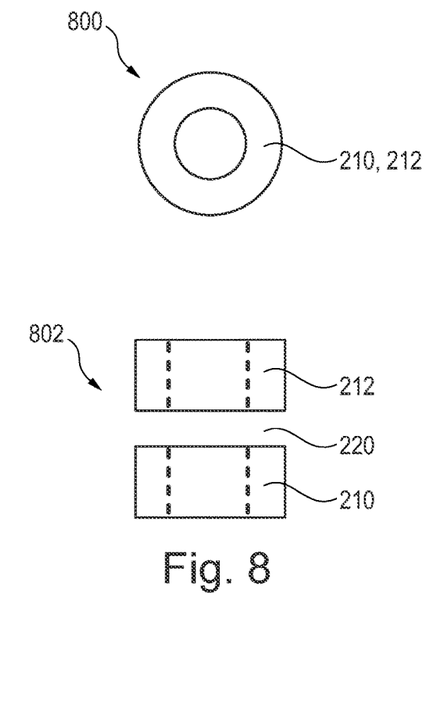
FIG. 8 illustrates a plan view and a side view of force transmission magnets implemented in fluidic valves according to an exemplary embodiment of the invention.
Figure 9:
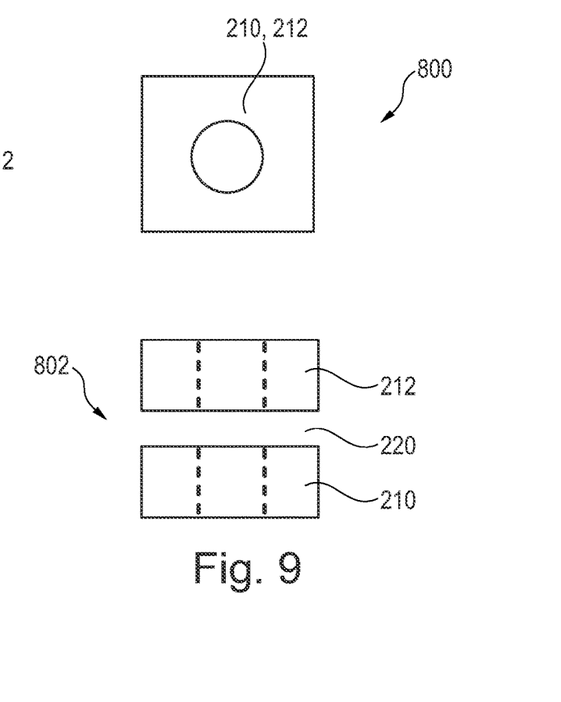
FIG. 9 illustrates a plan view and a side view of force transmission magnets implemented in fluidic valves according to another exemplary embodiment of the invention.

FIG. 8 and FIG. 9 illustrate embodiments of force transmission elements 210, 212 in a plan view 800 and in a side view 802 implemented according to exemplary embodiments of the invention. In the configuration according to FIG. 8, the permanent magnets constituting the force transmission elements 210, 212 have a cylindrical shape. Such a configuration is advantageous and specifically allows for a compact configuration. In the configuration according to FIG. 9, the permanent magnets constituting the force transmission elements 210, 212 have a cuboid shape. Such a configuration geometrically increases the active magnetic area.

Figure 10:
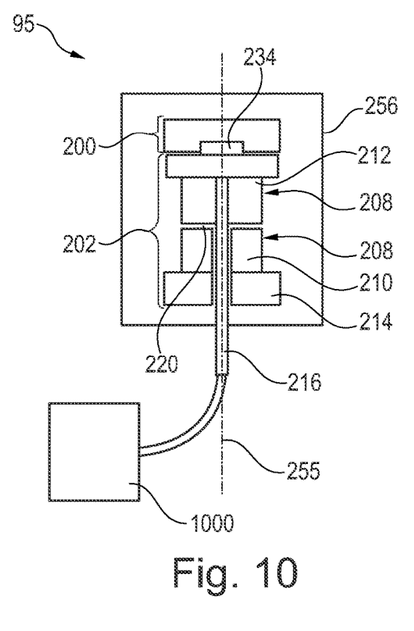
FIG. 10 illustrates a cross-sectional view of a fluidic valve according to another exemplary embodiment of the invention.

FIG. 10 illustrates a cross-sectional view of a fluidic valve 95 according to an exemplary embodiment of the invention. In addition to the components which have been already explained above referring to FIG. 2, the embodiment of FIG. 10 additionally shows an electric motor 1000 driving the rotatable rotor shaft 216. FIG. 10 illustrates that there is no contact between the moving parts other than the contact surface between the stator 200 and the rotor 202.

Figure 11:
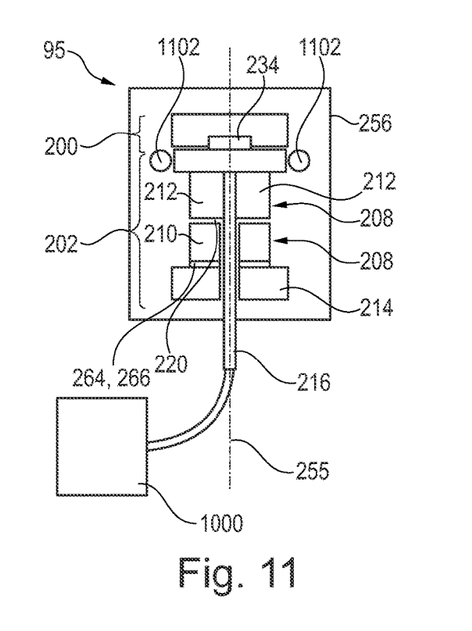
FIG. 11 illustrates a cross-sectional view of a fluidic valve according to another exemplary embodiment of the invention.

FIG. 11 illustrates a cross-sectional view of a fluidic valve 95 according to another exemplary embodiment of the invention.

The embodiment of FIG. 11 differs from the embodiment according to FIG. 10 in that a bearing 1102 is shown. Furthermore, a force adjustment mechanism 264, 266 is implemented, as explained above.

Figure 12:
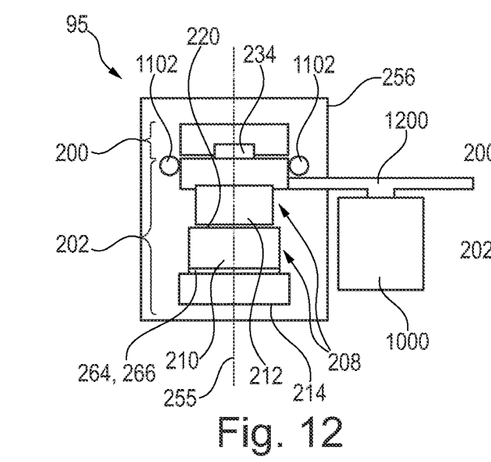
FIG. 12 illustrates a cross-sectional view of a fluidic valve according to another exemplary embodiment of the invention.

FIG. 12 illustrates a cross-sectional view of a fluidic valve 95 according to yet another exemplary embodiment of the invention.

The embodiment of FIG. 12 differs from the embodiment according to FIG. 11 in that no rotor shaft 216 is implemented in the embodiment of FIG. 12. Instead of this, FIG. 12 comprises a rotatable lateral gear mechanism 1200 configured for rotating the mobile part of the rotor 202 and being arranged laterally of the force transmission elements 210, 212. According to FIG. 12, the rotatable lateral gear mechanism 1200 is configured as gear wheel driven by electric motor 1000.

Figure 13:
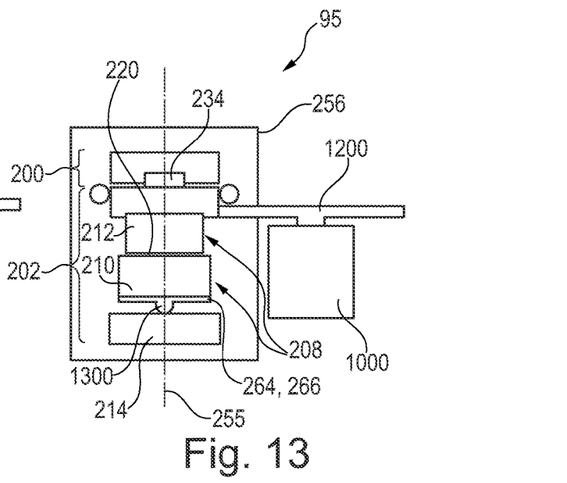
FIG. 13 illustrates a cross-sectional view of a fluidic valve according to another exemplary embodiment of the invention.

FIG. 13 illustrates a cross-sectional view of a fluidic valve 95 according to still another exemplary embodiment of the invention.

The embodiment of FIG. 13 differs from the embodiment according to FIG. 12 in that a pivotal bearing 1300 is additionally implemented.

Figure 14:
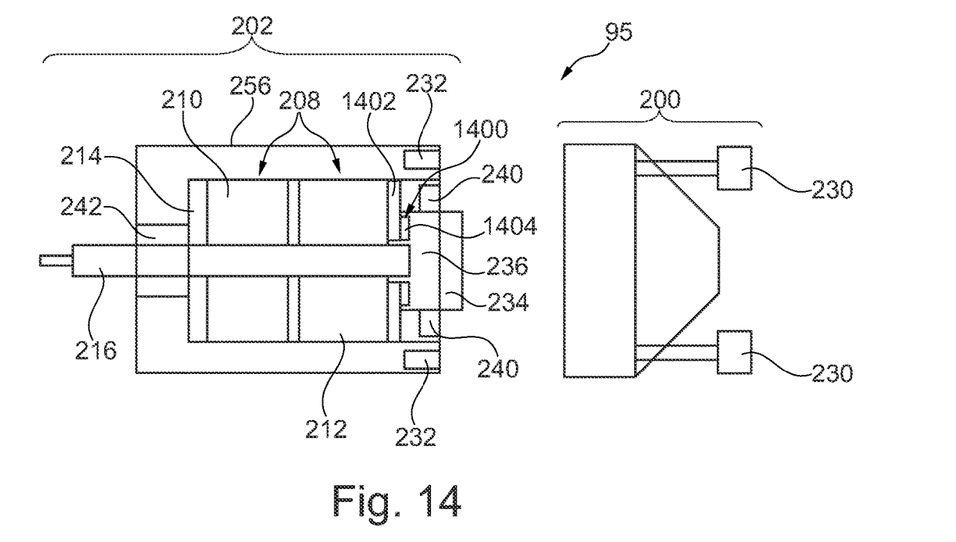
FIG. 14 illustrates a cross-sectional view of a fluidic valve according to another exemplary embodiment of the invention.

FIG. 14 illustrates a cross-sectional view of a fluidic valve 95 according to still another exemplary embodiment of the invention.

The embodiment of FIG. 14 differs from the embodiment according to FIG. 2 in that a low friction interface 1400 is additionally implemented. More specifically, the fluidic valve 95 of FIG. 14 comprises the low friction interface 1400 arranged between a seal member (composed of rotor seal 234 and seal keeper 236) and the force transmission mechanism 208. Furthermore, the low friction interface 1400 is configured for enabling a low friction mutual motion between the seal member (see reference numerals 234, 236) and the force transmission element 212. More specifically, the low friction interface 1400 of FIG. 14 comprises a first low friction body 1402 on the foremost force transmission element 212 and, in contact therewith, a second low friction body 1404 on the seal keeper 236. The first low friction body 1402 may be embodied as a disk glued (or otherwise firmly attached) on the front surface of the force transmission element 212 and cooperating with a further firmly attached or freely running disk on the back surface of the seal keeper 236. The first mentioned disk may be made of a hard metal with a hardening coating (such as DLC coated steel or low friction coated tungsten carbide). The further disk may be made of plastic or alternatively may be made of one of the aforementioned materials. The materials of the disk and of the further disk may be exchanged. The disc and the further disc may be tribologically matched to enable a low friction mutual motion between force transmission element 212 and seal keeper 236. Although a dry coupling between the force transmission element 212 and the seal keeper 236 is possible with the described low friction interface 1400, it is optionally possible to further reduce friction by additionally providing a contact surface between the disc and the further disk with oil or grease or some other lubricant. According to FIG. 14, a low friction and low wear system is provided enabling the seal keeper 236 to rotate on the force adjustment magnet in form of the force transmission element 212.

Figure 15:
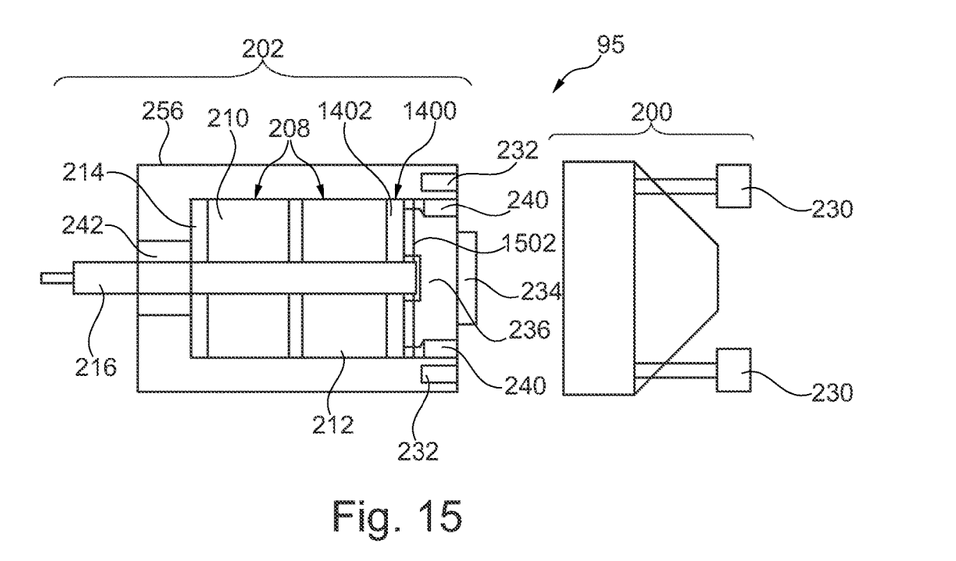
FIG. 15 illustrates a cross-sectional view of a fluidic valve according to another exemplary embodiment of the invention.

FIG. 15 illustrates a cross-sectional view of a fluidic valve 95 according to yet another exemplary embodiment of the invention.

The embodiment of FIG. 15 differs from the embodiment according to FIG. 14 in that, according to FIG. 15, the low friction interface 1400 is embodied as a low friction body 1402 (which may be embodied as in FIG. 14) on the foremost force transmitting element 212 and, in contact therewith, a roller bearing 1502 (or any other axial bearing) between the low friction body 1402 and the seal keeper 236. For example, the roller bearing 1502 may be a needle roller. According to FIG. 15, the seal keeper 236 runs on the axial roller bearing 1502. A contact surface of the seal keeper 236 may be hardened. According to FIG. 15, a low friction and low wear system is provided by introducing an axial bearing between the rotor seal keeper 236 and the low friction body 1402 attached to the force transmission element 212.

It should be noted that the term "comprising" does not exclude other elements or features and the term "a" or "an" does not exclude a plurality. Also elements described in association with different embodiments may be combined. It should also be noted that reference signs in the claims shall not be construed as limiting the scope of the claims.

The invention claimed is:

1. A fluidic valve for switching between different fluid coupling states, the fluidic valve comprising:
   a stator having at least one fluidic stator interface;
   a rotor having at least one fluidic rotor interface, wherein the rotor is rotatable relative to the stator to thereby switch the fluidic valve between a plurality of different fluid coupling states between the at least one fluidic stator interface and the at least one fluidic rotor interface;
   a force transmission mechanism configured for pressing the stator and the rotor together by a contactless force transmission to provide for a fluid tight sealing between the stator and the rotor, wherein:
      the force transmission mechanism comprises cooperating force transmission elements configured for generating a pressing force for pressing the stator and the rotor together; and
      the force transmission mechanism is mounted in the fluidic valve and configured for performing an equilibration motion for at least partially equilibrating an axial misalignment between the stator and the rotor; and
   a rotatable lateral gear mechanism configured for rotating at least part of the rotor and being arranged laterally of the force transmission elements.

2. The fluidic valve of claim 1, wherein all force transmission elements are mounted in the rotor.

3. The fluidic valve of claim 1, wherein the force transmission elements are configured as magnets.

4. The fluidic valve of claim 3, wherein the magnets are arranged for generating the pressing force by a mutually repelling magnetic force between the magnets.

5. The fluidic valve of claim 3, wherein the magnets are arranged with an axial gap in between, and wherein the gap is maintained by a magnetic force between the magnets.

6. The fluidic valve of claim 1, wherein one of the force transmission elements is fixedly mounted.

7. The fluidic valve of claim 6, wherein the fixedly mounted force transmission element is mounted axially more remotely from the stator than the floatingly mounted force transmission element.

8. The fluidic valve of claim 6, comprising a resilient element arranged between the fixedly mounted force transmission element and a casing of the rotor.

9. The fluidic valve of claim 1, wherein one of the force transmission elements is floatingly mounted.

10. The fluidic valve of claim 1, wherein adjacent ones of the force transmission elements are axially spaced from one another by a gap and are configured with a mutual form closure design so as to counteract axial misalignment between the force transmission elements.

11. The fluidic valve of claim 1, comprising a force adjustment mechanism configured for adjusting a pressing force provided by the force transmission mechanism.

12. The fluidic valve of claim 1, wherein the force transmission mechanism is a purely magnetic force transmission mechanism.

13. The fluidic valve of claim 1, comprising a feature selected from the group consisting of:
   the at least one fluidic stator interface is configured as at least one fluidic port;
   the at least one fluidic rotor interface is configured as at least one fluidic groove; and
   the rotor comprises a seal member comprising the at least one fluidic rotor interface, and the fluidic valve comprises a low friction interface arranged between the seal member and the force transmission mechanism and configured for enabling a low friction mutual motion between the seal member and at least part of the force transmission mechanism.

14. A fluid separation apparatus for separating a fluidic sample into a plurality of fractions, the fluid separation apparatus comprising:
   a fluid drive unit configured for driving a fluid comprising a mobile phase and the fluidic sample in the mobile phase along a fluidic path;
   a separation unit arranged within the fluidic path and configured for separating the fluidic sample into the plurality of fractions;
   a fluidic valve for switching between different fluid coupling states, the fluidic valve comprising:
      a stator having at least one fluidic stator interface;
      a rotor having at least one fluidic rotor interface, wherein the rotor is rotatable relative to the stator to thereby switch the fluidic valve between a plurality of different fluid coupling states between the at least one fluidic stator interface and the at least one fluidic rotor interface; and
      a force transmission mechanism configured for pressing the stator and the rotor together by a contactless force transmission to provide for a fluid tight sealing between the stator and the rotor; and
   an injector configured for injecting the fluidic sample into the mobile phase in the fluidic path by the fluidic valve.

15. The fluid separation apparatus of claim 14, further comprising a feature selected from the group consisting of:
   a detector configured to detect separated fractions of the fluidic sample;
   a fractioner unit configured to collect separated fractions of the fluidic sample;
   a data processing unit configured to process data received from the fluid separation apparatus; and
   a degassing apparatus for degassing the mobile phase.

16. A method for switching a fluidic valve between different fluid coupling states, the method comprising:
   rotating a rotor of the fluidic valve, comprising at least one fluidic rotor interface, relative to a stator of the fluidic valve, comprising at least one fluidic stator interface, to thereby switch the fluidic valve between a plurality of different fluid coupling states between the at least one fluidic stator interface and the at least one fluidic rotor interface;
   pressing the stator and the rotor together by a contactless force transmission to provide for a fluid tight sealing between the stator and the rotor; and
   performing an equilibration motion for at least partially equilibrating a misalignment between the stator and the rotor,
   wherein:
      the contactless force transmission is done by a force transmission mechanism mounted in the fluidic valve and comprising cooperating force transmission elements configured for generating a pressing force for pressing the stator and the rotor together; and the rotating is done by a rotatable lateral gear mechanism configured for rotating at least part of the rotor and being arranged laterally of the force transmission elements.

* * * * *